(12) United States Patent
Kronenthal

(10) Patent No.: US 10,058,159 B2
(45) Date of Patent: Aug. 28, 2018

(54) STERILE COMPOSITIONS FOR HUMAN COSMETIC PRODUCTS

(71) Applicant: Richard L. Kronenthal, Fair Lawn, NJ (US)

(72) Inventor: Richard L. Kronenthal, Fair Lawn, NJ (US)

(73) Assignee: Richard L. Kronenthal, Fair Lawn, NJ (US)

( * ) Notice: Subject to any disclaimer, the term of this patent is extended or adjusted under 35 U.S.C. 154(b) by 0 days.

(21) Appl. No.: 15/690,558

(22) Filed: Aug. 30, 2017

(65) Prior Publication Data
US 2018/0153276 A1 Jun. 7, 2018

Related U.S. Application Data

(60) Provisional application No. 62/459,645, filed on Feb. 16, 2017, provisional application No. 62/450,123, filed on Jan. 25, 2017, provisional application No. 62/428,679, filed on Dec. 1, 2016.

(51) Int. Cl.
| | | |
|---|---|---|
| *A45D 40/00* | (2006.01) | |
| *A61K 8/67* | (2006.01) | |
| *A61Q 19/00* | (2006.01) | |
| *A61L 2/08* | (2006.01) | |
| *B65D 75/36* | (2006.01) | |
| *B65D 35/44* | (2006.01) | |
| *B65D 75/58* | (2006.01) | |
| *A45D 33/34* | (2006.01) | |
| *A45D 34/04* | (2006.01) | |
| *A45D 40/26* | (2006.01) | |

(52) U.S. Cl.
CPC ......... *A45D 40/0087* (2013.01); *A45D 33/34* (2013.01); *A45D 34/04* (2013.01); *A45D 40/26* (2013.01); *A61K 8/678* (2013.01); *A61L 2/081* (2013.01); *A61L 2/087* (2013.01); *A61Q 19/00* (2013.01); *B65D 35/44* (2013.01); *B65D 75/36* (2013.01); *B65D 75/58* (2013.01); *A61K 2800/10* (2013.01); *A61K 2800/30* (2013.01); *A61K 2800/87* (2013.01); *A61L 2202/23* (2013.01)

(58) Field of Classification Search
CPC ........ B65D 35/44; B65D 75/36; B65D 75/58; A45D 33/34; A45D 40/0087; A45D 34/04; A45D 40/25; A45D 40/26; A61K 8/678; A61L 2/081; A61L 2/087
USPC ............................................. 206/581, 823
See application file for complete search history.

(56) References Cited

U.S. PATENT DOCUMENTS

| | | | | |
|---|---|---|---|---|
| 3,917,120 | A | * 11/1975 | Larenz | ................... B65D 75/48 206/484 |
| 4,512,475 | A | * 4/1985 | Federighi | ................ A61J 1/067 206/484 |
| 4,540,007 | A | 9/1985 | Carracoy | |
| 4,770,323 | A | 9/1988 | Debard | |
| 4,871,091 | A | * 10/1989 | Preziosi | ................ A61F 9/0008 206/438 |
| 5,123,925 | A | 6/1992 | Smestad et al. | |
| 5,713,381 | A | * 2/1998 | Sloane | ................. A45C 11/005 132/312 |
| 6,054,138 | A | 4/2000 | Trebosc et al. | |
| 6,177,115 | B1 | 1/2001 | Meyer | |
| 6,460,781 | B1 | * 10/2002 | Garcia | ................... A45D 37/00 222/107 |
| 6,997,219 | B2 | 2/2006 | Py et al. | |
| 8,501,091 | B2 | 8/2013 | Lopez et al. | |
| 8,747,741 | B2 | 6/2014 | Lopez et al. | |
| 9,408,455 | B2 | 8/2016 | Py | |
| 9,555,911 | B2 | 1/2017 | Pawlowski et al. | |
| 9,598,195 | B2 | 3/2017 | Deutschle et al. | |
| 2002/0086039 | A1 | 7/2002 | Lee et al. | |
| 2003/0088215 | A1 | 5/2003 | Ferguson et al. | |
| 2004/0001773 | A1 | 1/2004 | Schmidt | |
| 2004/0094449 | A1 | * 5/2004 | Schmid | ................... A61J 1/067 206/524.1 |
| 2006/0226043 | A1 | * 10/2006 | Smith | ..................... A61J 1/067 206/438 |
| 2007/0228073 | A1 | * 10/2007 | Mazzarino | ......... B65D 75/5811 222/107 |
| 2009/0017080 | A1 | 1/2009 | Tanner et al. | |

(Continued)

FOREIGN PATENT DOCUMENTS

EP 0 852 206 A1 7/1998

OTHER PUBLICATIONS

Reisch M S, entitled "Restrictions ramp up on cosmetic preservatives," C&EN, cen.acs.org, Nov. 28, 2016, pp. 18-20.
PCT Notification of Transmittal of the International Search Report and the Written Opinion of the International Searching Authority, or the Declaration dated Jan. 23, 2018 in connection with PCT International Patent Application No. PCT/US2017/60977, 9 pages.

*Primary Examiner* — Chun Cheung
(74) *Attorney, Agent, or Firm* — Amster, Rothstein & Ebenstein LLP

(57) ABSTRACT

Because antimicrobial preservatives used in virtually all cosmetics exhibit degrees of adverse human toxicity that have become of increasing concern, a three element system is disclosed that eliminates the need for cosmetic preservatives and their degradation fragments that may exhibit toxicity. Element 1 comprises a cosmetic formulation not containing any preservative components. Element 2 is an individual unit dose of an Element 1 cosmetic formulation in a microbially-impenetrable disposable container. Element 3 comprises the sterilization of the sealed unit dose disposable container, employing heat or, preferably, employing ionizing radiation.

19 Claims, No Drawings

(56) References Cited

U.S. PATENT DOCUMENTS

| | | | |
|---|---|---|---|
| 2009/0191138 A1* | 7/2009 | Dechow | A61K 8/042 |
| | | | 424/61 |
| 2009/0317430 A1* | 12/2009 | Cassin | A61K 8/466 |
| | | | 424/401 |
| 2010/0116772 A1* | 5/2010 | Teys | A45D 34/04 |
| | | | 215/228 |
| 2011/0045042 A1 | 2/2011 | Sasaki et al. | |
| 2011/0127188 A1* | 6/2011 | Thompson | B32B 27/08 |
| | | | 206/438 |
| 2014/0311941 A1 | 10/2014 | Zhang et al. | |
| 2015/0306259 A1 | 10/2015 | Deutschle et al. | |
| 2016/0311566 A1 | 10/2016 | Cocaud et al. | |

* cited by examiner

STERILE COMPOSITIONS FOR HUMAN COSMETIC PRODUCTS

CROSS-REFERENCE TO RELATED APPLICATIONS

This application claims the benefit of U.S. Provisional Patent Application Nos. 62/428,679, filed on Dec. 1, 2016, 62/450,123, filed on Jan. 25, 2017, and 62/459,645, filed on Feb. 16, 2017, the contents of all of which are herein incorporated by reference.

FIELD OF THE INVENTION

The instant invention allows the preparation of easily administered, sterile cosmetic formulations not containing preservatives. Such formulations remain hermetically sealed until immediately before use and, thus, are not exposed to air (oxygen). Thus, oxidative degradation is minimized and product stability is proportionately lengthened over that of products supplied in, e.g., jars that must be opened and closed as part of each cosmetic application.

BACKGROUND OF THE INVENTION

The Federal Food, Drug and Cosmetic Act defines cosmetics by their intended use, as "articles intended to be rubbed, poured, sprinkled or sprayed on, introduced into, or otherwise applied to the human body . . . for cleansing beautifying, promoting attractiveness, or altering the appearance." (FD&C Act, 21 U.S.C. § 321(i)). Among the products included in this definition are skin moisturizers, perfumes, lipsticks, fingernail polish, eye and facial makeup preparations, cleansing shampoos, permanent waves, hair colors and deodorants as well as any substance intended for use as a component of a cosmetic product. The European Union Directive (76/768/EEC) defines a "cosmetic product" as "any substance or preparation intended for placing in contact with the various external parts of the human body (epidermis, hair system, nails, lips and external genital organs) or with the teeth and the mucous membranes of the oral cavity with a view exclusively or principally to cleaning them, perfuming them or protecting them in order to keep them in good condition, change their appearance or correct body odors." (Art. 1.1).

Cosmetic preservatives may be defined as a chemical or substance that is added to cosmetics to prevent decomposition by microbial growth or by undesirable chemical changes, e.g., oxidation. According to the US FDA, some of the ways cosmetics may become contaminated with bacteria or fungi are: contaminated raw materials, water or other ingredients; poor manufacturing conditions; ingredients that encourage growth of microorganisms without an effective preservative system; packaging that does not protect a product adequately; poor shipping or storage conditions; and consumer use such as the need to dip fingers into the product. Thus, it is vital that contamination with pathogenic microorganisms be minimized or prevented entirely, and it is the elimination of such microorganisms that this patent application addresses.

Most cream-based products are marketed in lidded jars with instructions to gently apply a small amount to the face in an upward circular motion once or preferably twice daily. An example of this type of product is NuFinity All-In-One/Day & Night Anti-Ageing Treatment (NuFinity Naturals, San Antonio, Tex. 78258). It is evident from the NuFinity instructions for use that the product is intended to be removed from the jar by the finger(s), and no instructions are given to wash the hands or use sterile gloves or applicators during product application. In some products of this kind, small applicators are supplied by the manufacturer to remove the product from the jar instead of using fingers, but the sterility of these applicators may not have been validated.

Because such products can be contaminated with pathogenic microorganisms during manufacture or by pathogenic microorganisms residing on the fingers every time the product is used, it has long been judged necessary to include antimicrobial/antifungal preservative agents in cosmetic formulae—usually at least two such preservative compounds are included in ingredient lists, e.g., Methylparaben (an antibacterial) and Propylparaben (an antifungal) to prevent microbial contamination of the product and prevent or retard subsequent microorganism growth, thus helping to prevent potential skin or systemic infections. This problem is thought to be so serious by the US FDA that it will, beginning in December, 2016, post, on a quarterly basis, data extracted from cosmetic adverse event reports submitted to FDA by consumers and health care providers. From Jan. 1, 2004 through Sep. 30, 2016, 4,322 such reports were submitted to the FDA for cosmetic products.

In the United States, cosmetics must contain preservatives because the FDA requires that the products not be injurious to the user and because insurance companies would not cover products that are not preserved. Cosmetic products are not required to be sterile, but the main embodiment of the present invention is to provide sterile, single dose products and eliminate the need for preservatives. Surgical products commonly used in operating rooms, such as internally indicated surgical sutures, are delivered sterile (usually radiation, ethylene oxide or heat sterilized) in microbially impervious single-use packaging and do not contain preservatives that are unnecessary in sterile single use packages.

While parabens are "Generally Recognized As Safe" for cosmetic use by the US FDA, there have been reports of parabens causing weak estrogenic activity leading to decreased testosterone production in male rats associated with significant caudal epididymal sperm reserve and sperm concentration decreases and reduction in daily sperm production and efficiency (Oishi, et al., "Effects of Propyl Paraben on The Male Reproductive System," Food and Chemical Toxicology, 40, 1807 (2002)). Other reports concerning the toxicity of preservatives include, e.g., "Preservatives and Fragrances in Selected Consumer-Available Cosmetics and Detergents" (Yazar, et al., Contact Dermatitis, 64, 265 (2011)), which discusses skin-sensitization; and "Decreased Sperm Number and Motile Activity of the F1 Offspring Maternally Exposed to Butyl Paraben", (Kang, et al., J. Vet. Med. Sci., 64, 227 (2002)), which discusses the significant decrease in both the number of pups born alive and surviving for 20 days from mothers receiving injections of 200 mg/kg of butyl paraben as were the lower weights of testes, seminal vesicles and prostate glands of F1 male offspring. In summary, maternal exposures to butyl paraben have adverse effects on the male offspring but not on the reproductive organs of the female offspring. See also "Urinary Concentrations of Parabens and Serum Hormone Levels, Semen Quality Parameters, and Sperm DNA Damage" (Meeker, et al., Environmental Health Perspectives, 119.2, 252 (2011)). There are many more such reports, two of which are listed below, that further substantiate these problems: "Possible endocrine disrupting effects of parabens and their metabolites" (Boberg, et al., J. Reproductive Toxicology, 30 301 (2010)); and "Assessment of Principal Parabens Used in Cosmetics After Their Passage Through Human Epidermis-dermis Layers" (El Hussein, et al., Experimental Dermatology, 16, 830 (2007)).

A useful overview of the severity of the current preservative situation entitled, "Restrictions Ramp Up On Cosmetic Preservatives," was authored by M. Reisch in the Nov. 28, 2016 issue of Chemical & Engineering News, pages 18-20. Reisch quotes the Chief Executive Officer of International Cosmetics & Regulatory Specialists as saying preservatives are meant "to keep cosmetics safe throughout their useful life from production until the last bit is used at the bottom of the jar." She fears that, over time, bacteria will build up resistance to the diminishing number of preservative options now available and does not see alternatives such as single-use or aseptic packaging as realistic—both because of the additional cost and because of the increased packaging waste. Thus, an expert who is highly skilled in the art, clearly teaches away from claims in the instant invention involving terminally sterilized single dose packaging.

The above overview also indicates the perception of severity of preservative toxicity by a group named the Green Chemistry and Commerce Council (GC3) that is creating a monetary prize competition for novel preservative concepts to accelerate the commercialization of new, safe and effective preservative systems. Such new systems also are to be biodegradable, free of carcinogen and endocrine disruption concerns and not likely to build microbial resistance. Among the 17 contest supporters, those that agreed to be named include Beiersdorf, Dow Chemical, Johnson & Johnson, Lonza, Target and Walmart. Thus, a group of large companies teaches away from sterilization and believes the solution to preservative toxicity is best based on new preservative technologies rather than on the sterilization of single dose cosmetic products not containing any added preservatives, as exemplified in this patent application.

Swinwood, et al., "Treatment of Cosmetics Ingredients With Gamma Radiation: A Market Development View", International J. of Radiation Applications and Instrumentation, Part C. Radiation Physics and Chemistry, 35, 369 (1990) focused on the use of gamma radiation for the reduction of microbial loads in certain cosmetic raw materials but did not consider or suggest the terminal sterilization of finished, packaged single dose cosmetic formulations. Swinwood's cosmetic products would still require preservative additives.

According to the Breast Cancer Fund, info@breastcancerfund.org, "In the U.S., major loopholes in federal law allow the cosmetics industry to put thousands of synthetic chemicals into personal care products, even if those chemicals are linked to cancer, infertility or birth defects."

Several US patents, e.g., U.S. Pat. No. 5,920,075, U.S. Pat. No. 5,221,563, U.S. Pat. No. 5,495,236, 4,786,812, U.S. Pat. No. 5,029,252 and U.S. Pat. No. 5,466,289 have been granted claiming the use of ultraviolet sterilization devices. However, such devices and their use are not claimed in the instant patent application because ultraviolet radiation will not penetrate the surfaces of opaque, sealed packaging materials as does gamma or electron beam radiation or heat. To be effective, UV rays must touch the surface of the micro-organism and so these UV-generator patents are not relevant to this invention.

U.S. Pat. No. 8,501,091 describes methods for heat sterilizing cosmetic products which comprise two different viscosities at two different regulated pressures and then aseptically cooling and packaging the combined product in a sterile atmosphere. A novel embodiment of the instant application discloses terminal thermal steam sterilization under pressure (autoclaving) and cooling in a sealed package.

A company in France, Pierre Fabre Laboratories, developed what they termed "Sterile Cosmetics" in 1996 and describes their production process in a company brochure as follows:

A. Sterilization of all cosmetic production equipment
B. Control of selected raw materials
C. Production of the cosmetic in a sterilized mixer (not a sterilizer mixer)
D. Innovative sterilization methods (not disclosed)
E. Packaging in a class A sterile environment
F. Training of production staff (sterile production requires specific expertise).

It is clear from this description that Pierre Fabre's products are manufactured and packaged aseptically and are not terminally sterilized in sealed packages by heat or by ionizing radiation exposure. Simply sterilizing mixing equipment does not necessarily sterilize cosmetic components being mixed in such equipment.

Using the Pierre Fabre process, a French company, Avene Dermatological Laboratories, marketed the first line of what was termed a "sterile" cosmetic product. Pierre Fabre also developed DEFI (Extreme Intact Formula Device), " . . . making it possible to protect sterile medicines from all germs in a large-capacity tube; the product remains sterile throughout use, with no risk of bacterial contamination." In 2009, two products were introduced by Avene in 50 ml DEFI tubes, clearly not single dose units. In 2011, a pediatric skin care product was launched by Avene in 50 ml DEFI tubes, and, in 2012, Avene launched two DEFI-based 50 ml products and that year, two 50 ml DEFI tube products were launched by A-Derma Dermatological Laboratories.

Thus, the direction taken to provide "sterile" cosmetics was to utilize the 50 ml DEFI multiple dose dispensing tubes. From Pierre Fabre Laboratories' publications, it is evident they did not consider combining single dose packaging with terminal radiation or other sterilization methods of single dose packaged cosmetics. Pierre Fabre Laboratories brochure goes on to state:

A. "The DEFI system helps preserve a completely intact sterile formula protected from all germs throughout the products use"
B. "No retro-contamination of the formula"
C. "Guaranteed sterile formula throughout entire use of the product."

Clearly, Pierre Fabre products are aseptically prepared and packaged without terminal sterilization.

A 50 ml. tube of AVENE Sterile Eau Thermale Skin Recovery Cream for hypersensitive and irritable skin containing 0% preservative, 0% fragrance and 0% alcohol was purchased with instructions to apply morning and evening (Laboratoires Dermatologiques Avene, 45, place Abel-Gance, 92100 Boulogne, Paris-France). The package has a flat, circular plastic surface about 1.25 inches in diameter at the center of which is an orifice about $\frac{1}{16}$ inch in diameter through which the reportedly sterile product is expelled by squeezing the attached 50 ml. tube. The user wipes the expelled product from the circular surface of the package, which leaves a thin, unpreserved layer of product exposed to viable bacteria until the next application, which transfers the contaminated product together with the next application. During this period, the sterile product containing no preservative or alcohol will be a site of bacterial proliferation. While the product in the tube is protected from contamination by a proprietary, unidirectional exit valve, it is contaminated by multi-hour exposure on the flat, circular plastic surface.

With the widespread use of anti-microbial preservatives such as, e.g., the parabens and chlorohexidine in cosmetic and cosmeceutical (i.e., formulations having drug-like effects or claims but not requiring FDA approval or clearance) formulations, it is evident that microbial (bacterial and fungal) contamination is an important issue and, because of potential adverse effects of such materials on the body as described in the literature cited above, it would be of advantage to safely eliminate their inclusion in cosmetics entirely.

Another disadvantage of manually dispensing an agent from a container such as a jar is that the actual optimum dose may not be accurately dispensed each time, depending upon the amount of product digitally transferred from the jar by a single individual from time to time or differences in amounts of the same material dispensed by different individuals.

The long felt need for cosmetic products with improved safety profiles is highlighted by the following report in Chemical & Engineering News, May 1, 2017, page 14: "Prize money available for new preservatives ($175,000) with improved environmental health and safety profiles for use in personal care and household products. The contest, operated by InnoCentive and the Green Chemistry & Commerce Council, is sponsored by Proctor & Gamble, Johnson & Johnson, and other firms. They are seeking broad-spectrum or single-action agents that control Gram-positive bacteria, Gram-negative bacteria, yeast, and mold or that act as preservative boosters. View contest details on line at . . . "

The present invention addresses the need for cosmetic products that are free of preservatives and at the same time, safe, sterile and convenient to use.

The disclosures of the publications mentioned herein are hereby incorporated by reference in their entireties into the subject application to more fully describe the art to which the subject application pertains.

SUMMARY OF THE INVENTION

The invention provides cosmetic products comprising a sterile, sealed, single dose package that is impermeable to microorganisms and air; and a sterile cosmetic formulation contained within the package; wherein the package and formulation do not contain an antimicrobial additive or a molecular fragment of an antimicrobial additive.

DETAILED DESCRIPTION OF THE INVENTION

The instant invention is based on a novel combination of three elements. The first element is the elimination of all preservatives from the formulation. The second element requires that the preservative-free cosmetic product of element one be packaged as a single unit dose to be used for one application and any remaining product discarded. The last element requires that the packaged single dose cosmetic product be sterilized in the package, preferably using ionizing radiation.

In one embodiment, the cosmetic product comprises:
a sealed, single dose package that is impermeable to microorganisms and air comprising a cosmetic formulation within the package;
wherein the cosmetic formulation does not contain an antimicrobial additive or a molecular fragment of an antimicrobial additive, and
wherein the product is gamma-radiation or electron beam sterilized.

In one embodiment, the cosmetic product comprises:
a sealed, single dose package that is impermeable to microorganisms and air comprising a cosmetic formulation within the package;
wherein the cosmetic formulation does not contain an antimicrobial additive or a molecular fragment of an antimicrobial additive, but does comprise at least one free radical scavenger, and
wherein the product is gamma-radiation or electron beam sterilized.

In one embodiment, the cosmetic product comprises:
a sealed, single dose package that is impermeable to microorganisms and air comprising a cosmetic formulation within the package;
wherein the cosmetic formulation does not contain an antimicrobial additive or a molecular fragment of an antimicrobial additive,
wherein the package comprises a metal foil or a metal foil plastic laminate, and
wherein the product is gamma-radiation or electron beam sterilized.

In one embodiment, the cosmetic product comprises:
a sealed, single dose package that is impermeable to microorganisms and air comprising a cosmetic formulation within the package;
wherein the cosmetic formulation does not contain an antimicrobial additive or a molecular fragment of an antimicrobial additive, but does comprise at least one free radical scavenger,
wherein the package comprises a metal foil or a metal foil plastic laminate, and
wherein the product is gamma-radiation or electron beam sterilized.

In one embodiment, the cosmetic product comprises:
a sealed, single dose blister package that is impermeable to microorganisms and air comprising a cosmetic formulation within the package;
wherein the cosmetic formulation does not contain an antimicrobial additive or a molecular fragment of an antimicrobial additive, but does comprise at least one free radical scavenger,
wherein the package comprises a metal foil or a metal foil plastic laminate, and is heat-sealed, and
wherein the product is gamma-radiation or electron beam sterilized.

In one embodiment, the formulation contains at least one free radical scavenger. In one embodiment, the free radical scavenger comprises a vitamin E ester.

In one embodiment, the package comprises a metal foil or a metal foil plastic laminate. In one embodiment, the package is a blister package that is heat-sealed.

In one embodiment, the formulation is expressible from the package by mechanical compression or by manual squeezing after the package is opened. In one embodiment, the package comprises a plastic dispenser. In one embodiment, the package comprises a removable cap that can be removed to release the formulation. In one embodiment, the package comprises a sealed tubular extension that can be cut off to release the formulation.

In one embodiment, the package comprises a single dose syringe dispenser contained in a foil or plastic outer package, where the syringe comprises one or more barrels or barrel compartments. In one embodiment, the syringe comprises more than one barrel or barrel compartments and a mixing-dispensing component attached to the distal end of the syringe.

In one embodiment, the sealed package and formulation contained within the package have been radiation-sterilized using gamma rays from a cobalt 60 source or by a sterilizing electron beam apparatus. In one embodiment, the sealed package and the formulation contained within the package have been radiation sterilized using x-rays. In one embodiment, the sealed package is gas permeable and the gas permeable sealed package and formulation contained within the package have been sterilized using super critical carbon dioxide. In one embodiment, the gas permeable sealed package and the formulation contained within the package have been sterilized using nitrogen dioxide. In one embodiment, the sealed package and formulation contained within the package have been heat-sterilized using an autoclave, microwave radiation, Pasteurization, or combinations thereof. In one embodiment, the formulation has been sterilized in bulk and aseptically transferred to a presterilized empty package, and the formulation-containing sterile package is then aseptically sealed.

In one embodiment, the formulation is in the form of a powder, liquid, cream, soft wax, solution, lotion, salve, paste, emulsion, or putty. In one embodiment, the formulation is selected from the group consisting of a skin moisturizer, skin wrinkle reducer, skin lotion, discolored skin area reducer, skin cleanser, skin exfoliant, skin depilatories, perfume, cologne, a fragrance, a lipstick, a nail polish, an eye make-up preparation, an eye shadow preparation, a make-up remover, a body powder, a foundation, a rouge, a sun block, an artificial (sunless) sun tan preparation, a shampoo, a permanent wave hair formulation, a hair color formulation, a gel, and a deodorant, and combinations thereof.

In one embodiment, the cosmetic formulation is impregnated in a porous carrier material prior to package sealing and sterilization, where the porous carrier material serves as an aid to application of the sterile cosmetic. In one embodiment, for improved application, the cosmetic products are impregnated into a porous carrier material such as a sponge, woven, knitted, non-woven fabric or a disposable brush comprising fibers or sponge on one end of a supporting member. This embodiment allows application of the sterile cosmetic without the need for employing user's fingers. Such carrier materials also may be packaged and sterilized separately from the cosmetic and combined at the time of use.

In one embodiment of this invention, the sealed product is ionizing radiation-sterilized, e.g., using a validated gamma ray exposure of, e.g., 25 kGy. The product dosage is controlled by sealing a constant amount of product corresponding to an optimum dose, e.g., 2.8 cc. or gm., in a plastic or, preferably, in a foil pouch that can be easily torn, peeled or cut open and the entire contents mechanically or manually expelled and applied to the skin after which the used container with any un-expelled cosmetic content is discarded.

In the orthopedic industry, implants such as artificial joints and allograft bone are commonly sterilized using either ethylene oxide or gamma radiation. Newer methods of sterilization have more recently been developed but are not yet widely used. Such methods are discussed by M. Barbella (worldwideweb.odtmag.com/issues/2015-02-01/view_features/comingclean/) and involve methods employing sub-critical carbon dioxide ($SCCO_2$), nitrogen dioxide ($NO_2$) or x-ray. Advantages of using $SCCO_2$ is that while it can provide sterilizing 6-log reduction of microorganisms, it does not degrade radiation-susceptible components, is chemically inert, easily removed from the product and is not toxic. Potential disadvantages of $SCCO_2$ for cosmetic applications are cost and the need for gas-permeable packaging that may require a gas-impermeable overwrap package. In one embodiment, $SCCO_2$ is an excellent candidate for terminal cosmetic sterilization.

Nitrogen dioxide sterilization developed by Noxilizer, Inc. involves its RTS 360 Industrial $NO_2$ Sterilizer, which uses nitrogen dioxide gas which is non-carcinogenic and nonflammable. Possible disadvantages include relatively small production lots for cosmetic applications. However, there is a need to sterilize expensive cosmetics not produced in large lots and, in another embodiment, $NO_2$ gas is applicable to this need.

X-radiation is an alternative to gamma sterilization. Ion Beam Applications S.A. offers contract x-ray sterilization services for medical products. X-rays will penetrate full pallets of product better than gamma rays which are less concentrated, an advantage for high volume cosmetic production. Synergy Health, plc in Daeniken, Switzerland developed a large scale x-ray sterilization unit based on a 700 kW Rhodotron electron beam accelerator that can process up to 80,000 pallets annually, a useful embodiment for terminally sterilizing large quantities of cosmetics.

In another embodiment, a syringe-like package may be used to contain the product. The syringe may be of a single barrel if one composition is indicated or a multiple barrel or compartmentalized single barrel syringe with an optional mixing-dispensing device attached to the distal end of the syringe if multiple components are to be mixed prior to application. For example, an anhydrous mixture not physically or chemically stable in the presence of water can be contained in one syringe compartment while water or buffer or saline or an aqueous gel can be contained in a second compartment and mixed together while being expelled from the syringe. This arrangement can avoid the separation of water from incompatible oil components during product aging.

In another embodiment, the container may have a cap or uncapped but sealed tubular extension on one end that may be cut or screwed off to release a constant weight or volume of the single dose product.

In one embodiment, preservatives are completely eliminated from the formulation and the sealed single use container containing the product is radiation sterilized which allows a sterile product to be applied each time the product is used. This embodiment also prevents exposure to air which may cause oxidative degradation of susceptible cosmetic components thus shortening shelf-life.

Other embodiments allow the use of other methods of sterilization such as heat [e.g., autoclave (e.g., 15 lbs of steam pressure for 15-20 minutes) if the product contains even small quantities of water], Pasteurization, i.e., rapid heating followed by rapid cooling, microwave radiation of foil or plastic packages containing the cosmetic, less desirable ethylene or propylene oxide exposure and electron beam radiation as alternatives to preferred gamma radiation.

In certain embodiments, if radiation-sterilization is employed, physiologically-safe free radical scavengers, e.g., d,l-tocopheryl acetate (vitamin E acetate), may optionally be added to the formulation.

Among the types of skin products contemplated by this invention are sterile moisturizing, anti-aging, anti-wrinkle, anti-viral (e.g., Shingles) anti-inflammatory, anti-pain (e.g., sunburn, chemical and thermal burns), anti-acne and anti-infectives, anti-neoplastics (e.g., chemotherapeutic drugs), post-natal stretch mark removal and post-operative skin therapies to avoid hypertrophic scars (e.g., keloids), Some of these examples are classified as drugs requiring FDA-approval rather than as cosmetics.

The cosmetic products can include within the formulation any of the ingredients for cosmetic formulations recognized in the art, such as for example, but not limited to, one or more of castor oil, a castor oil derivative, a dye, a pigment, a silicone, a mineral, iron oxide, talc, zinc oxide, a natural oil or fat, and a modified natural oil or fat. The formulation, for example, can be in the form of a powder, liquid, cream, soft wax, solution, lotion, salve, paste, emulsion, putty or aerosol spray.

In an optional embodiment, preservative(s) can be left in the radiation-sterilized product as an extra measure of safety should a package containing the cosmetic be unknowingly damaged or otherwise sterility-compromised.

In one version of any of the embodiments disclosed herein, the cosmetic product comprises a sealed, single dose package that is impermeable to microorganisms and optionally impermeable to air, comprising a cosmetic formulation within the package, wherein the cosmetic formulation does not contain an antimicrobial additive or a molecular fragment of an antimicrobial additive, and wherein the product is gamma-radiation or electron beam sterilized.

All combinations of the various elements described herein are within the scope of the invention unless otherwise indicated herein or otherwise clearly contradicted by context.

The invention also includes methods of making the cosmetic products disclosed herein, as well as methods of using the cosmetic products.

Prophetic Example 1

A commercially available hand cream indicated for helping to heal dry, cracked hands, listed on the jar's label among its ingredients, propylparaben, sodium benzoate and imidazolidinyl urea, all antimicrobial preservatives. This product, is formulated as closely as possible without the three preservatives and samples heat-sealed in foil blister packages and irradiated in a cobalt 60 source at a sterilizing gamma dose of 25 kGy (2.5 mrads). Comparative testing of the sterilized samples according to the label directions, "Apply as needed especially after hand washing," does not distinguish any qualitative efficacy differences between the samples containing or without containing the listed preservatives.

What is claimed is:

1. A cosmetic product which comprises:
 a sealed, single dose package that is impermeable to microorganisms and air comprising a cosmetic formulation within the package;
 wherein the cosmetic formulation does not contain an antimicrobial additive or a molecular fragment of an antimicrobial additive, and
 wherein the product is sterile.

2. The cosmetic product of claim 1, wherein the formulation contains at least one free radical scavenger.

3. The cosmetic product of claim 1, wherein the package comprises a metal foil or a metal foil plastic laminate.

4. The cosmetic product of claim 2, wherein the package comprises a metal foil or a metal foil plastic laminate.

5. The cosmetic product of claim 4, wherein the package is a blister package that is heat-sealed.

6. The cosmetic product of claim 1, wherein the package comprises a plastic dispenser.

7. The cosmetic product of claim 1, wherein the formulation is expressible from the package by mechanical compression or by manual squeezing after the package is opened.

8. The cosmetic product of claim 1, wherein the package comprises a single dose syringe dispenser contained in a foil or plastic outer package, wherein the syringe comprises one or more barrels or barrel compartments.

9. The cosmetic product of claim 8, wherein the syringe comprises more than one barrel or barrel compartments and a mixing-dispensing component attached to the distal end of the syringe.

10. The cosmetic product of claim 1, wherein the package comprises a removable cap that can be removed to release the formulation.

11. The cosmetic product of claim 1, wherein the package comprises a sealed tubular extension that can be cut off to release the formulation.

12. The cosmetic product of claim 1, wherein the sealed package and formulation contained within the package have been radiation-sterilized using gamma rays from a cobalt 60 source.

13. The cosmetic product of claim 1, wherein the formulation has been sterilized in bulk and aseptically transferred to a presterilized empty package, and the formulation-containing sterile package is then aseptically sealed.

14. The cosmetic product of claim 2, wherein the free radical scavenger comprises a vitamin E ester.

15. The cosmetic product of claim 1, wherein the formulation is in the form of a powder, liquid, cream, soft wax, solution, lotion, salve, paste, emulsion, or putty.

16. The cosmetic product of claim 1, wherein the formulation is selected from the group consisting of a skin moisturizer, skin wrinkle reducer, skin lotion, discolored skin area reducer, skin cleanser, skin exfoliant, skin depilatories, perfume, cologne, a fragrance, a lipstick, a nail polish, an eye make-up preparation, an eye shadow preparation, a make-up remover, a body powder, a foundation, a rouge, a sun block, an artificial (sunless) sun tan preparation, a shampoo, a permanent wave hair formulation, a hair color formulation, a gel, and a deodorant, and combinations thereof.

17. The cosmetic product of claim 1, wherein the cosmetic formulation is impregnated in a porous carrier material prior to package sealing and sterilization, where the porous carrier material serves as an aid to application of the sterile cosmetic.

18. The cosmetic product of claim 1, wherein the product is radiation sterilized.

19. The cosmetic product of claim 1, wherein the product is gamma-radiation or electron beam sterilized.

* * * * *